(12) United States Patent
Glenn et al.

(10) Patent No.: US 6,368,351 B1
(45) Date of Patent: Apr. 9, 2002

(54) INTERVERTEBRAL SPACE IMPLANT FOR USE IN SPINAL FUSION PROCEDURES

(76) Inventors: Bradley J. Glenn, 3455 LaPlaya Dr., Davis, CA (US) 95616; Gary A. Schneiderman, 1810 Ladino Rd., Sacramento, CA (US) 95864

( * ) Notice: Subject to any disclaimer, the term of this patent is extended or adjusted under 35 U.S.C. 154(b) by 0 days.

(21) Appl. No.: 09/819,461

(22) Filed: Mar. 27, 2001

(51) Int. Cl.[7] .................................................. A61F 2/44
(52) U.S. Cl. ..................................... 623/17.15; 606/61
(58) Field of Search ........................... 623/17.15, 17.16, 623/17.11, 17.14; 606/61, 60, 53; 411/55

(56) References Cited

U.S. PATENT DOCUMENTS

| | | |
|---|---|---|
| 4,714,469 A | 12/1987 | Kenna |
| 4,917,704 A | 4/1990 | Frey |
| 5,507,816 A | 4/1996 | Bullivant |
| 5,554,191 A | 9/1996 | Lahille |
| 5,653,763 A | 8/1997 | Errico |
| 5,658,336 A | 8/1997 | Pisharodi |
| 5,723,013 A | 3/1998 | Jeanson |
| 5,782,832 A | 7/1998 | Larsen |
| 5,800,550 A | 9/1998 | Sertich |
| 5,865,848 A | 2/1999 | Baker |
| 5,893,890 A | 4/1999 | Pisharodi |
| 5,989,291 A | * 11/1999 | Ralph et al. ............. 623/17.15 |
| 6,045,579 A | * 4/2000 | Hochshuler et al. ..... 623/17.15 |
| 6,102,950 A | 8/2000 | Vaccaro |
| 6,162,252 A | * 12/2000 | Kuras et al. ............. 623/17.15 |
| 6,190,414 B1 | * 2/2001 | Young et al. ............. 623/17.15 |
| 6,193,757 B1 | * 2/2001 | Foley et al. .............. 623/17.16 |

* cited by examiner

Primary Examiner—Pedro Philogene
(74) Attorney, Agent, or Firm—Heisler & Associates

(57) ABSTRACT

An implant assembly 10 is provided for surgical implantation into an intervertebral space S, such as for stabilization of vertebrae V adjacent the intervertebral space S during a spinal fusion procedure. The implant assembly 10 includes a primary segment 20 separate from a secondary segment 60. These segments 20, 60 are elongate and of sufficiently small cross-section that they can be implanted posteriorly in a minimally invasive manner. The segments 20, 60 preferably have a rectangular cross-section so that they can be inserted on a side into the intervertebral space S and then rotated into a maximum height orientation to widen the intervertebral space S. The segments 20, 60 interlock together at an intersection there between. The primary segment 20 preferably includes a tunnel 30 and the secondary segment 60 preferably includes a neck 70 with the tunnel 30 and neck 70 sized complementally so that the segments 20, 60 stabilize each other where they intersect with the neck 70 within the tunnel 30. The entire implant assembly 10 is thus provided which both widens and supports the intervertebral space S and is sufficiently rigid to provide adequate support for the intervertebral space S as the vertebrae V are fusing together. The segments 20, 60 are fitted with height expansion systems which can be accessed after implantation of the segments 20, 60 so that height of the segments 20, 60 can be further increased, particularly at distal ends 26, 66 of the segments 20, 60, such that the intervertebral space S can be provided with a desirable amount of lordosis.

20 Claims, 6 Drawing Sheets

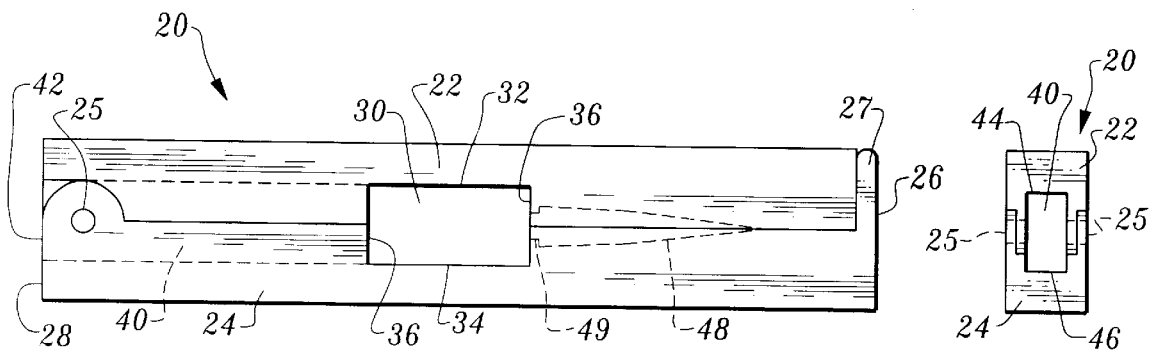
Fig. 6
Fig. 8
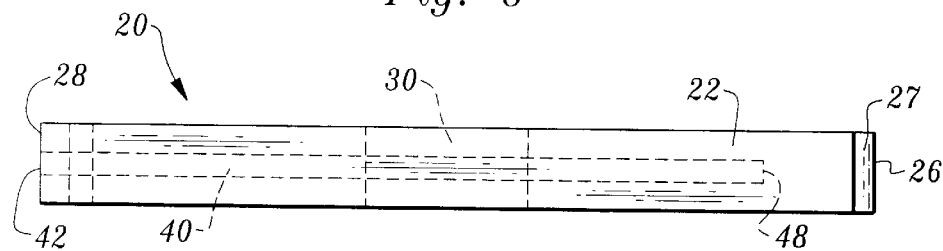
Fig. 7
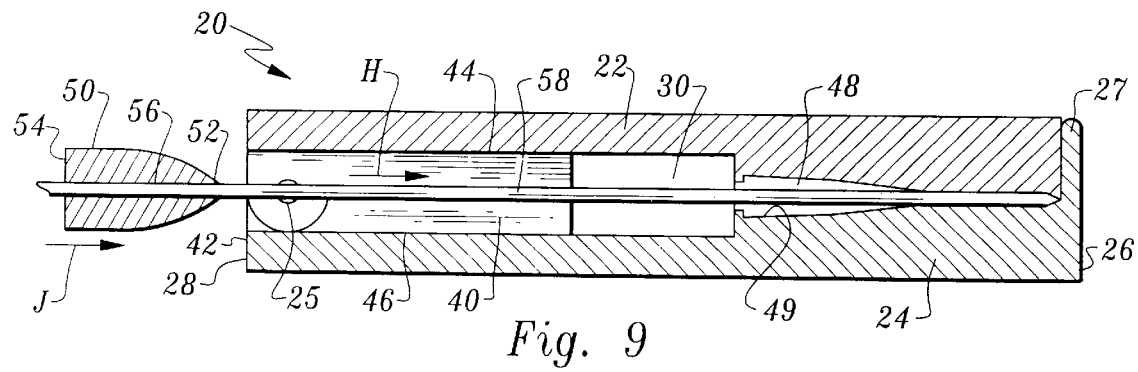
Fig. 9
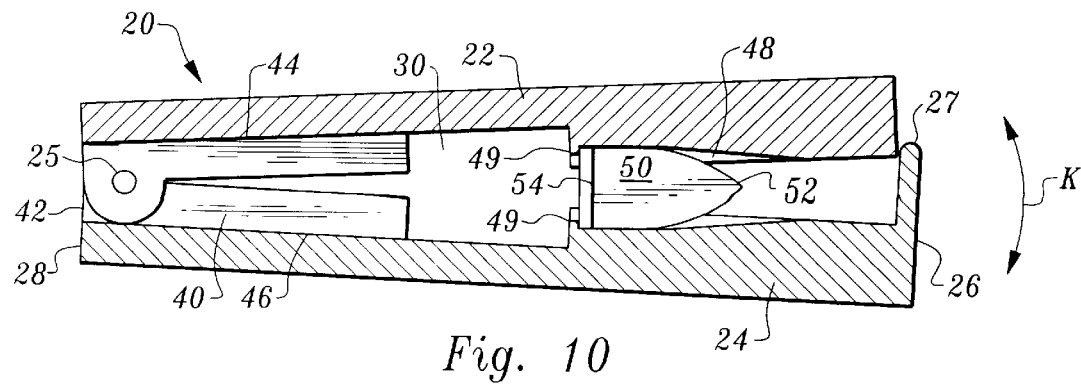
Fig. 10

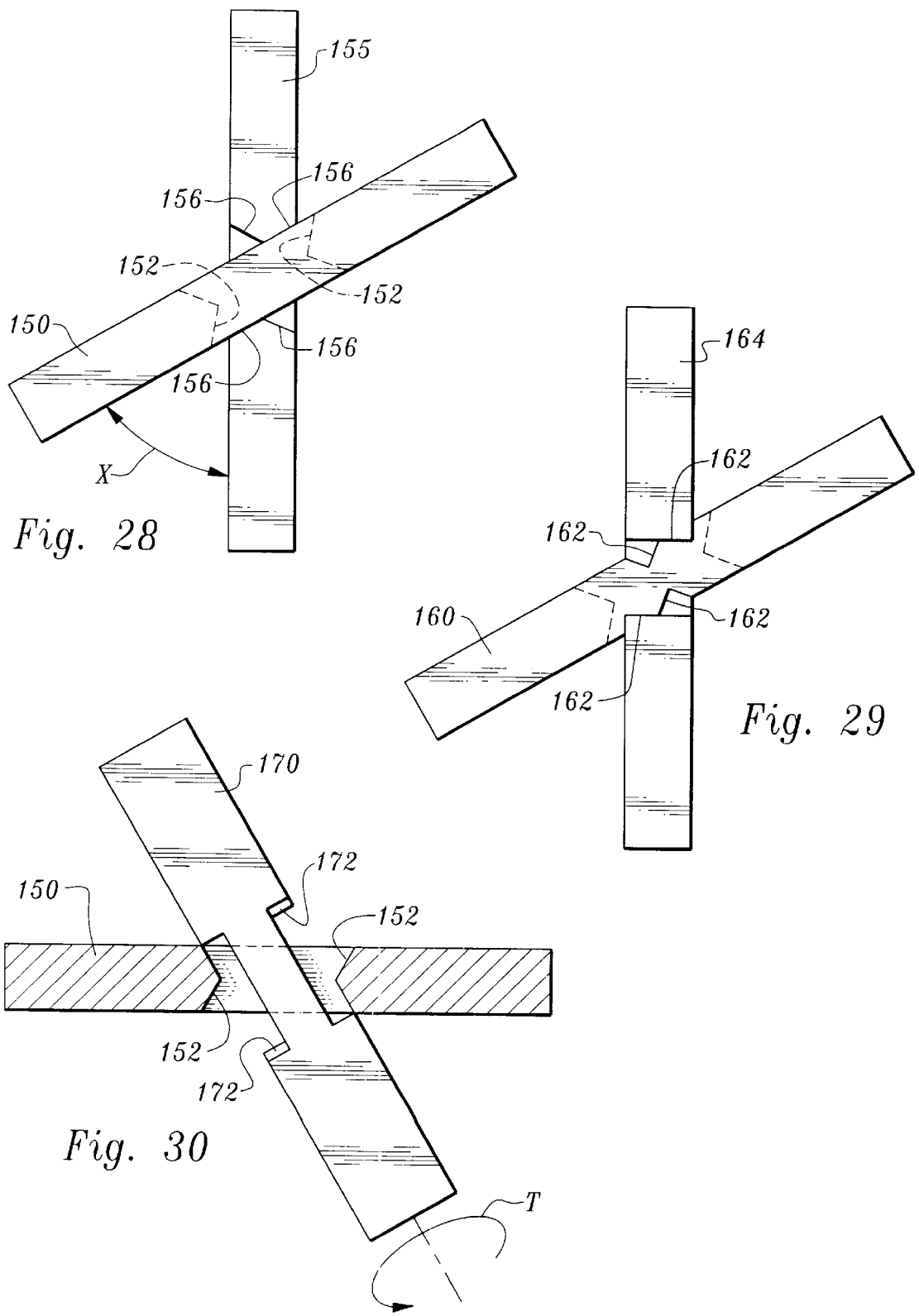

INTERVERTEBRAL SPACE IMPLANT FOR USE IN SPINAL FUSION PROCEDURES

FIELD OF THE INVENTION

The following invention relates to implants which are configured to be placed within an intervertebral space between adjacent spinal vertebrae after a disk has been removed from the space and to facilitate fusion of the vertebrae together. More particularly, this invention relates to implants which can be implanted posteriorly in either a minimally invasive or open manner and spread vertebrae adjacent the intervertebral space away from each other to recreate the lumbar lordosis and support the vertebrae while they fuse together.

BACKGROUND OF THE INVENTION

Spinal fusion procedures are known as an effective treatment for certain spinal conditions. In general, such spinal fusion procedures may involve removal of a disk within an intervertebral space between two adjacent vertebrae. After the disk has been removed an implant can be located within the intervertebral space to push the vertebrae apart. By pushing the vertebrae apart, ligaments and other body structures surrounding the vertebrae are placed in tension and tend, along with the implant, to securely hold the two vertebrae in fixed position relative to each other. It is important to restore as much as possible the height of the intervertebral space. It is also important to restore the angle or "lordosis" of the intervertebral space. Finally, fusion material is placed within the intervertebral space which induces bone growth within the intervertebral space, effectively fusing the two vertebrae together with the implant typically remaining embedded within this fused vertebra combination.

Placement of the implant within the intervertebral space is accomplished in one of two general ways. First, the intervertebral space can be accessed anteriorly by performing abdominal/thoracic surgery on the patient and accessing the intervertebral space from a front side of the patient. In this anterior procedure major abdominal/thoracic surgery is typically involved. However, the intervertebral space can be generally accessed anteriorly, such that the risk of injury to the nerves is generally reduced and the surgeon has greater flexibility in positioning the implant precisely where desired.

Second, the implant can be inserted posteriorly. Direct posterior access to the intervertebral space requires moving the spinal nerves within the spinal canal towards the midline and can result in nerve injury or scarring. Implantation in the intervertebral space can also be accessed from a location spaced to the left or right side of the spinal column and at an angle extending into the intervertebral space. This approach avoids the spinal canal. A minimally invasive method using small incisions can be used but is must be carefully performed to avoid sensitive spinal structures. Additionally, implants of a smaller size are typically required due to the small amount of clearance between vertebral structures. Hence, the amount of spreading of the vertebrae with a posterior implant is often less than adequate. Additionally, portions of the vertebrae typically need to be at least partially carved away to provide the access necessary to insert the implants posteriorly into the intervertebral space.

Implants for the intervertebral space come in a variety of different configurations, most of which are designed for anterior implantation. One known prior art implant is described in detail in U.S. Pat. No. 5,800,550 to Sertich. The Sertich implant is configured to be implanted posteriorly and comes in two pieces. Two separate incisions are made on either side of the spine and the pieces of the overall implant are inserted generally parallel to each other, but can be angled slightly away from a parallel orientation. The Sertich implant pieces have a rectangular cross section and an elongate form. The pieces are initially implanted with a lesser dimension oriented vertically so that the pieces can easily enter the intervertebral space. The pieces are then rotated 90° so that the greater dimension is rotated to vertical, tending to spread the vertebrae vertically to enlarge the intervertebral space.

The implant taught by Sertich is not entirely desirable. Because the Sertich implant involves two entirely separate pieces, they do not stabilize each other in any way and hence provide a less than ideal amount of vertebral stabilization. Additionally, the relatively parallel angle at which they are implanted typically requires removal of portions of the vertebrae and retraction of the spinal nerves to properly implant the pieces of the Sertich implant. If the two pieces of the implant are angled more towards each other, they tend to decrease further in the stability that they provide to the vertebrae. Also, the Sertich implant pieces have a size which requires a relatively large incision to insert into the intervertebral space.

Accordingly, a need exists for a posteriorly placed intervertebral space implant which has a small cross-sectional profile at insertion and yet can provide a large amount of displacement between adjacent vertebrae once placed. The implant must expand sufficiently far apart to restore the height of the intervertebral space and act substantially as a single rigid structure within the intervertebral space after implantation is completed. Such an invention would additionally benefit from being capable of having a greater height in an anterior region such that lordosis can be achieved in an amount desired by the surgeon with an anterior side of the intervertebral space larger than a posterior side of the intervertebral space.

SUMMARY OF THE INVENTION

This invention is an intervertebral space implant which is configured to be implanted posteriorly in a minimally invasive or open surgical procedure. The implant includes two separate segments including a primary segment and a secondary segment. The primary segment and the secondary segment enter the intervertebral space through separate incisions on either side of the spine and along paths which intersect within the intervertebral space. To enhance a spreading of the intervertebral space with the implant, the segments have a height between a bottom surface and a top surface which is greater than a lateral width. The segments can thus be introduced into the intervertebral space with the top and bottom surfaces spaced laterally from each other and then be rotated 90° so that the top surface is above the bottom surface and a height of the segments is maximized.

Portions of the primary segment and the secondary segment adjacent where the segments intersect are removed to allow the segments to lie in a substantially common plane. Preferably, the primary segment includes a tunnel passing laterally through the primary segment near a midpoint thereof. The secondary segment is provided with a neck near a midpoint thereof which has a lesser height than other portions of the secondary segment. The tunnel is sized so that the secondary segment can pass through the tunnel in the primary segment and then be rotated with the neck of the secondary segment within the tunnel of the primary segment.

After the secondary segment has been rotated the two segments are interlocking together in a crossing pattern forming the implant assembly of this invention. Hence, the implant assembly of this invention provides the advantage of having a relatively low profile for insertion posteriorly in a minimally invasive manner and yet results in an overall implant assembly which has separate segments interlocking together to form a single substantially rigid implant assembly to maximize stabilization of the vertebrae adjacent the intervertebral space.

Additionally, the segments are formed in a manner which facilitates height expansion of the segments after implantation, especially at distal ends of the segments. Such additional height expansion further stabilizes vertebrae adjacent the intervertebral space and provides lordosis to the intervertebral space.

Specifically, the primary segment is preferably formed with a top structure separate from a bottom structure which pivot relative to each other, such as about a hinge. A passage passes between the top structure and the bottom structure. A shim can pass along the passage and cause a distal end of the primary segment to be expanded in height when the shim enters a tapering end portion of the passage. The distal end of the primary segment is thus expanded in height to an extent desired by a surgeon to provide a desirable amount of "lordosis" for the spinal fusion procedure.

Similarly, the secondary segment is preferably formed from a top jaw and a bottom jaw which can pivot relative to each other, such as about a hinge. A bore passes between the top jaw and the bottom jaw and a wedge is caused to move within the bore in a manner causing the top jaw and the bottom jaw to be spaced apart and causing a height of the secondary segment to be increased at a first distal end of the secondary segment.

The insertion of the segments themselves as well as the movement of shims and wedges within the segments to enhance their height is all accomplished through a small posterior incision. A variety of different hinge arrangements, shim and wedge arrangements and other structural variations are provided for the segments of the implant assembly.

OBJECTS OF THE INVENTION

Accordingly, a primary object of the present invention is to provide an implant for an intervertebral space which can be implanted posteriorly and still provide a substantially rigid implant assembly for spreading and stabilization of the vertebrae adjacent the intervertebral space.

Another object of the present invention is to provide an implant assembly having separate segments which are as low profile as possible so that posterior implantation can be accomplished in as minimally invasive a surgical procedure as possible.

Another object of the present invention is to provide an implant assembly for an intervertebral space which is initially entered into the intervertebral space in separate segments which are later interlocked together.

Another object of the present invention is to provide an intervertebral space implant assembly which can be adjusted in height to maximize a size of the intervertebral space generally and to allow for selective height adjustment within different portions of the intervertebral space, to provide a surgeon with a maximum amount of flexibility in positioning vertebrae adjacent the intervertebral space as precisely as desired.

Another object of the present invention is to provide an implant assembly which can be located within an intervertebral space with little risk of damage to sensitive surrounding tissues.

Other further objects of the present invention will become apparent from a careful reading of the included drawing figures, the claims and detailed description of the invention.

BRIEF DESCRIPTION OF THE DRAWINGS

FIG. 6 is a side elevation view of a primary segment of the implant assembly with hollow interior details shown in broken lines.

FIG. 7 is a top plan view of that which is shown in FIG. 6.

FIG. 8 is a proximal end elevation view of that which is shown in FIG. 6.

FIG. 9 is a full sectional view of that which is shown in FIG. 6 and with a guide wire and shim of this invention shown entering a passage within the primary segment to expand a height of the primary segment adjacent a distal end of the primary segment.

FIG. 10 is a full sectional view of that which is shown in FIG. 9 after the shim has been fully advanced into the passage of the primary segment of this invention so that the height of the distal end of the primary segment has been enhanced.

FIGS. 28–30 are top plan views of alternatives of the implant assembly of this invention showing how various beveled surfaces and relief notches can be provided adjacent the tunnel in the primary segment and the neck in the secondary segment to facilitate rotation of the secondary segment within the tunnel of the primary segment and to facilitate orientation of the secondary segment at an angle relative to the primary segment other than purely a perpendicular angle.

DESCRIPTION OF THE PREFERRED EMBODIMENTS

Figure 1:
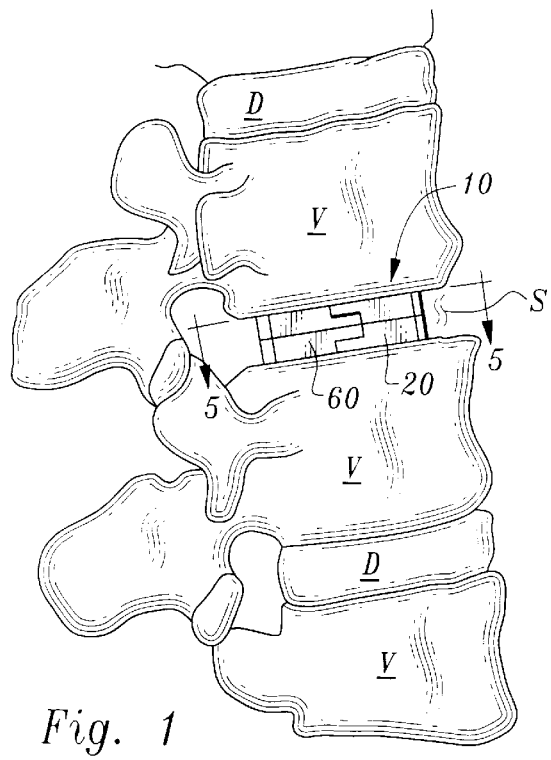
FIG. 1 is a side elevation view of a human spine with an intervertebral space containing the implant assembly of this invention.
Figure 2:
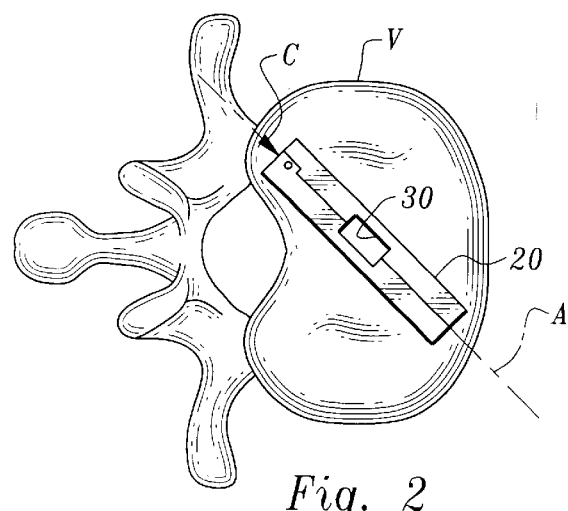
FIGS. 2–5 are top plan views taken along line 5—5 of FIG. 1 illustrating the four basic steps involved in the implantation of the implant assembly of this invention.
Figure 3:
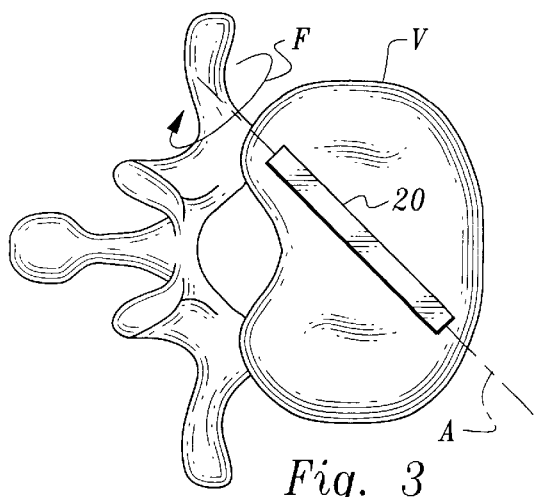

Referring to the drawings, wherein like reference numerals represent like parts throughout the various drawing figures, reference numeral 10 (FIG. 1) is directed to an implant assembly for implantation into an intervertebral space S between adjacent vertebrae V after a disk D has been removed from the intervertebral space S. A primary segment 20 and a secondary segment 60 are implanted along separate pathways but interlock together within the intervertebral space S to form a single implant assembly 10. The resulting assembly 10 securely stabilizes the vertebrae V adjacent the intervertebral space S for spinal fusion of the vertebrae V together.

Figure 4:
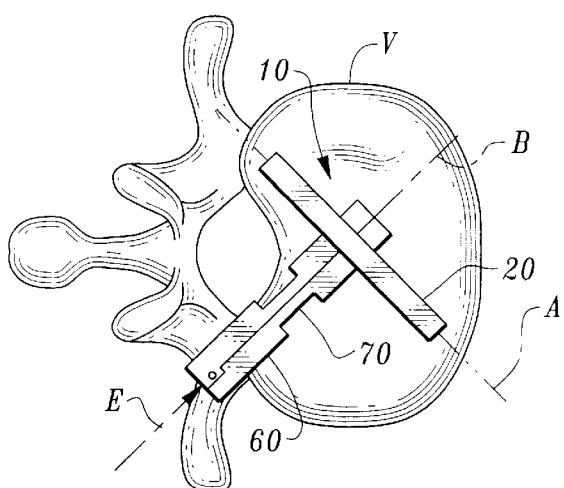

In essence, and with particular reference to FIGS. 1–5, the basic details of the implant assembly 10 are described. The implant assembly 10 includes a primary segment 20 (FIG. 2) and a secondary segment 60 (FIG. 4). The primary segment 20 is elongate in form extending along a primary axis A. The primary segment 20 is preferably higher than it is wide (compare FIG. 2 with FIG. 3), thus having a rectangular cross-section. The primary segment 20 can thus be inserted on its side into the intervertebral space (along arrow C of FIG. 2) and then rotated within the intervertebral space (along arrow F of FIG. 3) to help spread vertebrae V adjacent the intervertebral space S away from each other. The primary segment 20 additionally includes a tunnel 30 (FIG. 2) passing laterally through the primary segment 20.

The secondary segment 60 (FIG. 4) is elongate and has a contour generally similar to that of the primary segment 20. However, the secondary segment 60 includes a neck 70 rather than the tunnel 30 of the primary segment 20. The secondary segment 60 has a cross-sectional size similar to a size of the tunnel 30. This size allows the secondary segment 60 to be inserted along secondary axis B (in the direction identified by arrow E of FIG. 4) through the tunnel 30 in the primary segment 20. The secondary segment 60 can later be rotated (along arrow G of FIG. 5) in a manner similar to the rotation of the primary segment 20 so that a height of the secondary segment 60 is oriented vertically and maximizes a spacing of vertebrae V adjacent the intervertebral space S. The segments 20, 60 interlock together to form the implant assembly 10 with the segments 20, 60 stabilizing each other and allowing the implant assembly 10 to stabilize the intervertebral spaces in which the assembly 10 is implanted.

More specifically, and with particular reference to FIGS. 6–10, details of the primary segment 20 according to a preferred embodiment of this invention are described. The primary segment 20 is an elongate substantially rigid construct formed from a top structure 22 and a bottom structure 24 which are pivotably joined together, such with a hinge 25. The hinge 25 can take on many different forms to provide the basic function of allowing the top structure 22 and the bottom structure 24 to be pivoted relative to each other.

The primary segment 20 extends from a distal end 26 to a proximal end 28. A guide wire stop 27 can be optionally included with the bottom structure 24 at the distal end 26 and extend up beyond the top structure 22.

The tunnel 30 passes laterally through the primary segment 20 between a top surface and a bottom surface of the primary segment 20. The tunnel 30 includes a top 32 preferably substantially parallel to a bottom 34 and sides 36 extending between the bottom 34 and the top 32. The tunnel 30 preferably has dimensions similar to exterior dimensions of the primary segment 20 itself, but rotated 90°. The tunnel 30 is thus sized to allow secondary segments 60 with dimensions similar to the primary segment 20 to pass laterally through the tunnel 30 during formation of the implant assembly 10 of this invention within the intervertebral space S (FIGS. 1–5).

A passage 40 extends longitudinally within the primary segment 20 and between the top structure 22 and the bottom structure 24. The passage 40 includes an entrance 42 at the proximal end 28 of the primary segment. The passage 40 additionally includes a roof 44 preferably substantially parallel to and spaced from a floor 46. Preferably, the passage 40 has a constant cross-section from the entrance 42 to a location where the passage 40 intersects the tunnel 30. The passage 40 preferably continues beyond the tunnel 30 and toward the distal end 26 of the primary segment 20. However, portions of the passage 40 on a distal side of the tunnel 30 preferably taper to form a tapering end 48 of the passage 40. A step 49 is preferably located in the passage 40 directly adjacent the tunnel 30.

The passage 40 is configured to receive a shim 50 therein. The shim 50 (FIG. 9) preferably has a rectangular cross-section which generally fills the passage 40 (FIG. 8) so that the shim does not rotate. The shim 50 preferably includes a tip 52 which is of lesser height than a tail 54. A central pathway 56 preferably passes through the shim 50. A guide wire 58 can be passed entirely through the passage 40 up to the stop 27 (along arrow H of FIG. 9) and then the shim 50 threaded onto the guide wire 58. The shim 50 can then be easily advanced along the guide wire 58 (arrow J of FIG. 9) and directed into the passage 40. When the shim 50 reaches the tapering end 48 of the passage 40, with the assistance of an appropriate shim pushing tool, the shim 50 causes the top structure 22 and bottom structure 24 of the primary segment 20 to be expanded away from each other (about arrow K of FIG. 10) and a height of the primary segment 20 to be enhanced at the distal end 26 of the primary segment 20.

Such distal end 26 height expansion for the primary segment 20 is desirable in many cases to provide lordosis to the intervertebral space S. Specifically, lordosis is a orientation for the intervertebral space S where an anterior edge of the intervertebral space S has a greater height than a posterior edge of the intervertebral space S. Such lordosis can be provided to a varying degree depending on the desires of the medical practitioner. With this invention the shim 50 is advanced an amount desired through the passage 40 of the primary segment 20 to provide an amount of lordosis which is desirable in the judgment of the medical practitioner. The segment 20 can be custom designed to provide the lordosis desired or can be variably expandable for adjustment during implantation.

With particular reference to FIGS. 11–14, details of a preferred embodiment of the secondary segment 60 are described. The secondary segment 60 preferably has a general exterior contour similar to that of the primary segment 20. Also, the secondary segment 60 is preferably divided into a top jaw 62 and a bottom jaw 64 which are pivotably connected together, such as at a hinge 65. As with the primary segment 20, the hinge 65 can take on a variety of different configurations. The secondary segment 60 extends from a first distal end 66 to a second proximal end 68.

Figure 5:
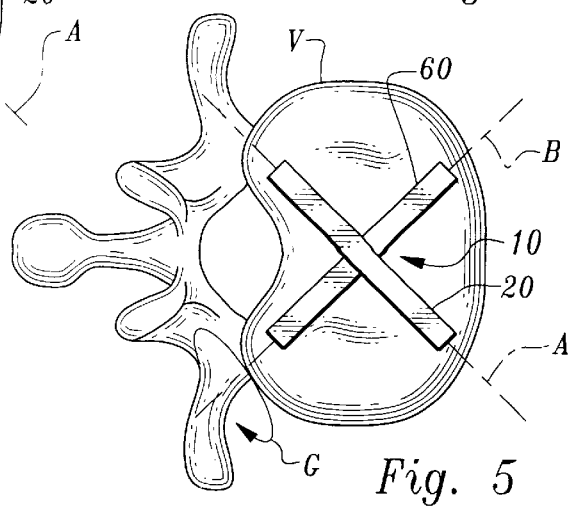
Figure 11:
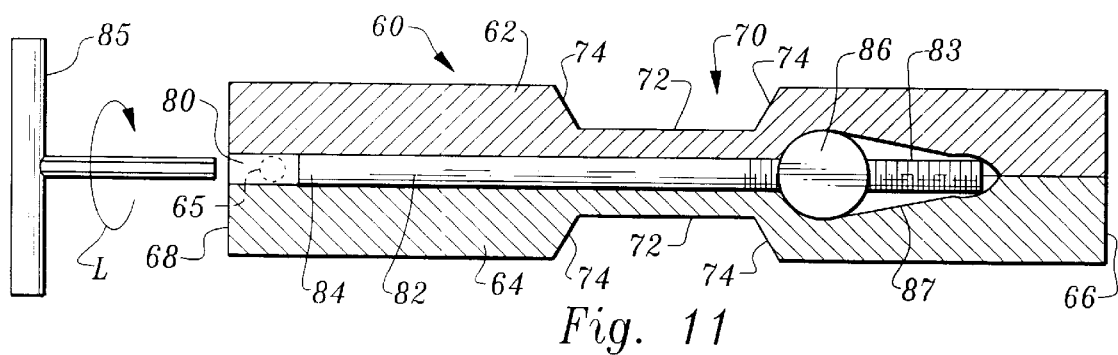
FIG. 11 is a full sectional side elevation view of a secondary segment of the implant assembly of this invention along with one form of a tool utilized to enhance a height of a distal first end of the secondary segment of the implant assembly of this invention.

The secondary segment 60 includes a neck 70 with two preferably substantially parallel surfaces 72 and side walls 74 extending between the parallel surfaces 72 of the neck 70 and top and bottom surfaces of the secondary segment 60. The side walls 74 can be perpendicular to the parallel surfaces 72 (as depicted generally in FIG. 4) or can be beveled (as shown in FIG. 11). The parallel surfaces 72 are located closer to each other than a distance between top and bottom surfaces of the secondary segment 60. The parallel surfaces 72 need not be precisely parallel, but benefit from having a lesser height than that of the top and bottom surfaces of the secondary segment 60 so that the neck 70 of the secondary segment 60 is an open region then can reside within the tunnel 30 or other open region in the primary segment 20 after rotation of the secondary segment 60 into an orientation with the top surface and the bottom surface vertically aligned along with top and bottom surfaces of the primary segment 20 (FIG. 5). Preferably, the neck 70 is located near a midpoint between the distal first end 66 and the proximal second end 68 of the secondary segment 60.

The width between lateral sides of the secondary segment 60 is preferably similar to a height of the neck 70 and a height of the tunnel 30 in the primary segment 20 for a tight fit within the tunnel 30 both before and after rotation (about arrow G of FIG. 5). The hinge 25 in the primary segment 20, general slight flexibility of the segments 20, 60 and possible slight additional clearances can provide the relief necessary to allow the secondary segment 60 to rotate with the neck 70 within the tunnel 30. Preferably, the secondary segment 60 tends to snap into its final position so that the segments 20, 60 are securely interlocked together.

To provide lordosis to the intervertebral space S, the secondary segment 60 is configured to allow height expansion, particularly at the distal first end 66. Specifically, the secondary segment 60 includes a bore 80 passing longitudinally from the proximal second end 68, at least part of the way toward the distal first end 66. The bore 60 includes a pin 82 therein which includes a threaded end 83 at an end thereof closest to the distal first end 66 of the secondary segment 60. An access end 84 of the pin 82 is opposite the threaded end 83 and closest to the proximal second end 68 of the secondary segment 60. A wrench 85 having one of a variety of different configurations (FIG. 11) can be utilized to cause the pin 82 to rotate by interaction of the wrench 85 with the access end 84 of the pin 82. Preferably, the bore 80 is slightly smaller adjacent the proximal end 68 to keep the pin 82 from sliding toward the proximal end 68 within the bore 80.

A wedge 86 is located within a tapering recess 87 in the bore 80. The wedge 86 is preferably cylindrical and includes a threaded hole extending perpendicularly through curving sides of the wedge into which the threaded end 83 of the pin 82 is located. Hence, when the pin 82 is rotated by rotation of the tool 85 (along arrow L of FIG. 11) the threaded end 83 of the pin 82 causes the wedge 86 to travel toward the distal first end 66 of the secondary segment 60 (along arrow M of FIG. 14). As the wedge 86 travels toward the distal first end 66 and through the tapering recess 87, the top jaw 62 and bottom jaw 64 are spread vertically (along arrow N of FIG. 14), enhancing a height of the secondary segment 60.

While the primary segment 20 and secondary segment 60 are shown with unique systems for vertically expanding top and bottom portions of the segments 20, 60, it is noted that these systems are merely one currently most preferred embodiments of a vertical height enhancement system for the segments 20, 60. In fact, a variety of different systems could be utilized to enhance the vertical height of the segments 20, 60 after implantation.

Figure 15:
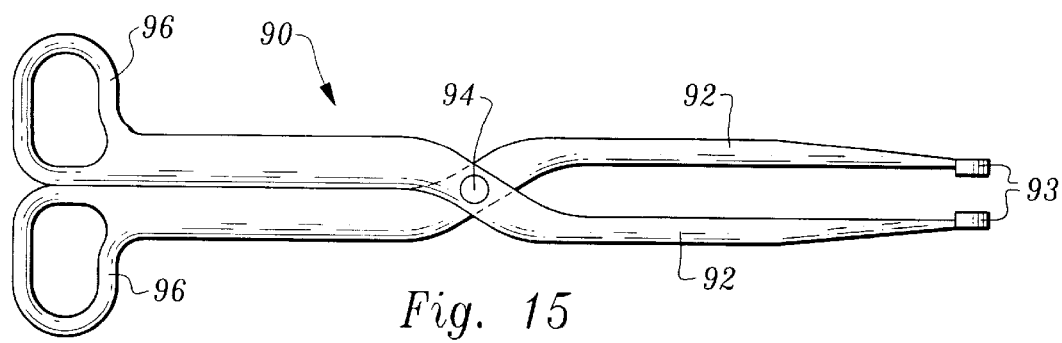
FIG. 15 is a top plan view of a tongs identifying one form of tool utilizable to implant the primary segment or the secondary segment of this invention.

Most preferably, the segments 20, 60 have a height between a top and bottom surface approximately twice a width between lateral sides of the segments 20, 60. A tongs 90 (FIG. 15) can be utilized to properly place the segments 20, 60 within the intervertebral space S (FIG. 1). Tongs 90 typically have fingers 92 which have tips 93 with a width similar to half of the lateral width of the segments 20. In this way, the segments 20, 60 could be grasped on lateral sides with the tips 93 of the fingers 92 of the tongs 90 and the segments 20, 60 can be advanced through a tubular cannula with the tubular cannula having a diameter similar to a height of the segments 20, 60 between top and bottom surfaces of the segments 20, 60. The tongs 90 might include a pivot 94 with handles 96 at ends of the tongs 90 opposite the fingers 92 for releasably grasping the segments 20, 60.

Alternatively, the segments 20, 60 could be grasped at their proximal ends 28, 68 through an appropriate attachment mechanism inboard of the top and bottom surfaces and lateral surfaces of the segments 20, 60 so that the tongs 90 or other placement tool would not add to a cross-sectional diameter needed for the cannula through which the segments 20, 60 would be passed.

Figures 12, 13:
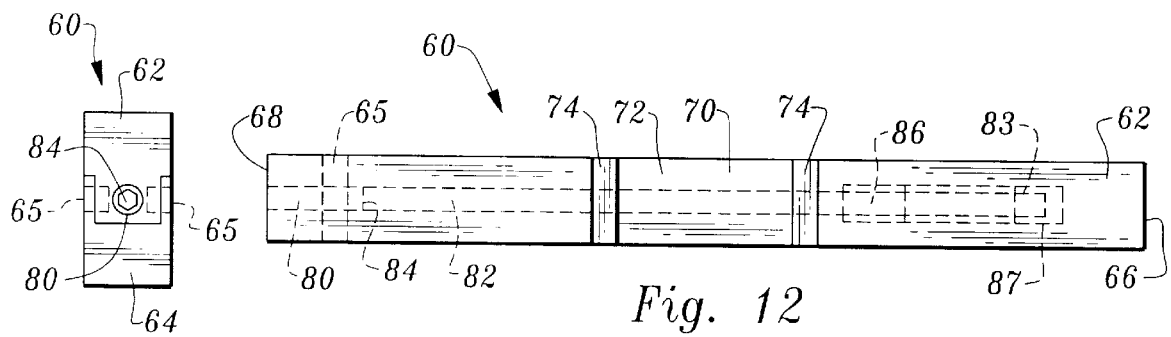
FIG. 12 is a top plan view of that which is shown in FIG. 11 with interior details shown with broken lines.
FIG. 13 is a proximal second end view of that which is shown in FIG. 12.
Figure 14:
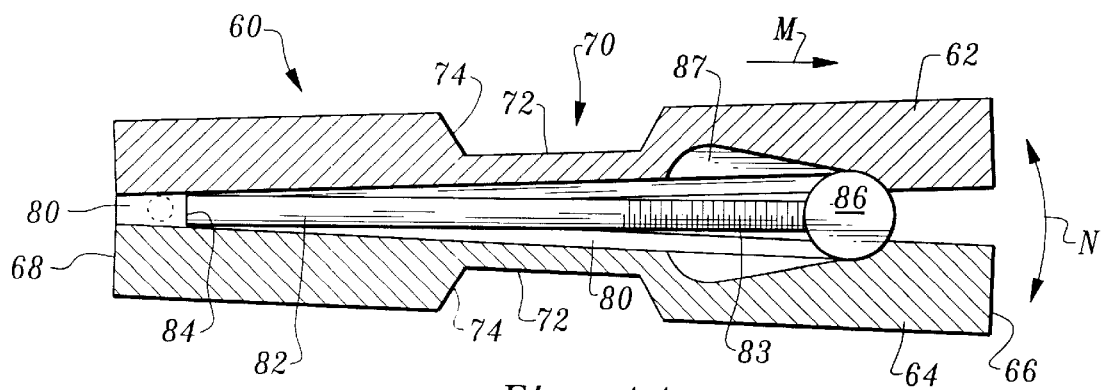
FIG. 14 is a full sectional view of that which is shown in FIG. 11 after a wedge has been fully advanced to enhance a height of the distal first end of the secondary segment.
Figure 16:
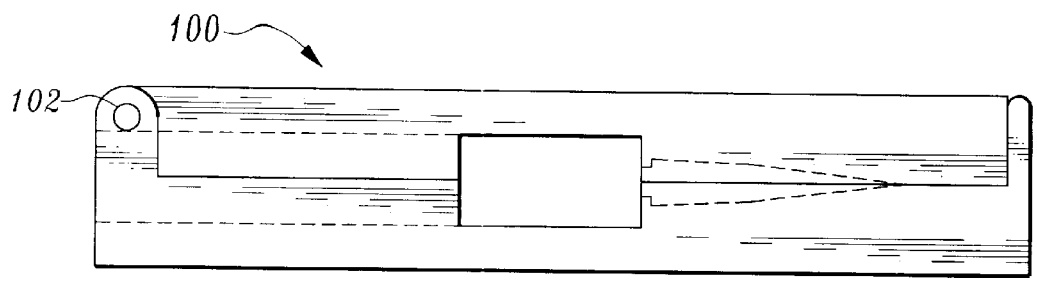
FIG. 16 is a side elevation view of an alternative embodiment of that which is shown in FIG. 6 showing an offset hinge.
Figure 17:
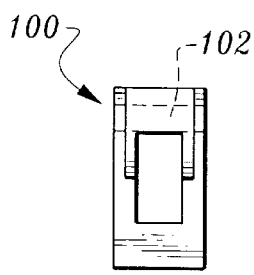
FIG. 17 is a proximal end view of that which is shown in FIG. 16.

With particular reference to FIGS. 16 and 17, details of an alternative offset hinge 102 are described. Such an offset hinge 102 is shown on a first alternative primary segment 100. However, the offset hinge 102 could similarly be located on a secondary segment such as a modification of the secondary segment 60 (FIGS. 11–14). The offset hinge 102 advantageously allows a single pintle to pass through all leaves of the offset hinge 102 (FIG. 17). The offset hinge 102 thus avoids the necessity of two partial pintles on opposite sides of a passage 40 (FIG. 8) or bore 80 (FIG. 13). Otherwise, the alternative primary segment 100 of FIGS. 16 and 17 is similar to the primary segment 20 of the preferred embodiment of the implant assembly 10 of this invention.

Figure 18:
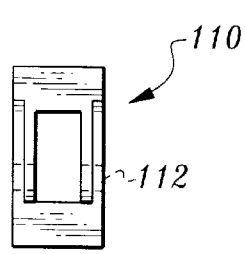
FIG. 18 is a proximal end view of a second alternative embodiment of the primary segment of this invention.

FIG. 18 shows a second alternative primary segment 110 featuring a split hinge 112. This split hinge 112 on the second alternative primary segment 110 is generally similar to the hinge 25 of the primary segment 20 of the preferred embodiment (FIG. 8). However, the overlapping leaves place the pintles of the split hinge 112 in a slightly different position. The second alternative primary segment 110 and split hinge 112 of FIG. 8 illustrate one of the many different hinge configurations which the segments 20, 60 of the implant assembly 10 of this invention can have to effectively allow top and bottom portions of the segments 20, 60 to move relative to each other.

While the material forming the segments 20, 60 would typically be some form of surgical grade bio-compatible stainless steel or other material, it is conceivable that the material forming the segments 20, 60 could be a form of hydrocarbon polymer or other plastic material, or a metallic material which has some appreciable flexibility characteristics. If the segments 20, 60 are made from such materials or can be machined to have sufficiently thin connection between the top and bottom portions of the segments 20, 60, the hinges 25, 102, 112 of the various embodiments of this invention could be replaced with the top and bottom portions of the segments 20, 60 merely flexing relative to each other sufficiently to allow the height expansion at the distal ends 26, 66 of the segments 20, 60 so that an appropriate amount of lordosis can be provided to the intervertebral space S (FIG. 1).

Figure 20:
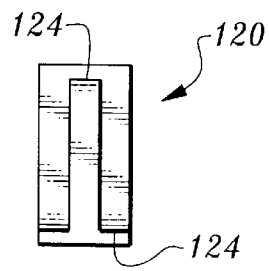
FIG. 20 is a distal end view of that which is shown in FIG. 19.
Figure 19:
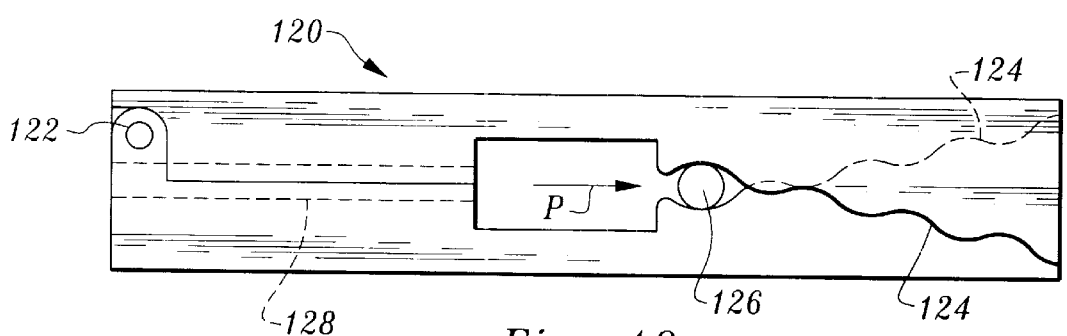
FIG. 19 is a side elevation view of a third alternative embodiment of a primary segment of the implant assembly of this invention with interior details shown with broken lines.
Figure 21:
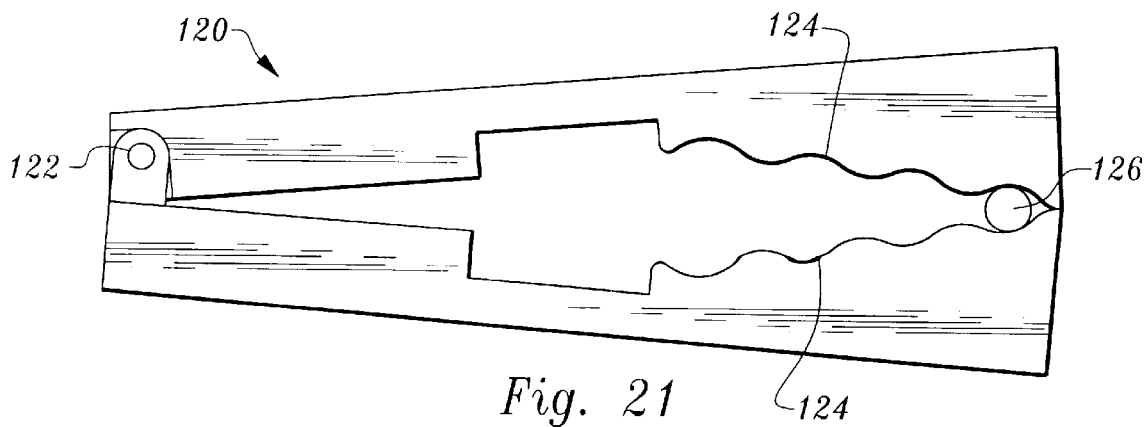
FIG. 21 is a side elevation view of that which is shown in FIG. 19 after full advancement of an alternative shim for use with the third alternative primary segment of the implant assembly of this invention.

With particular reference to FIGS. 19–21 details of a third alternative primary segment are described. This third alternative primary segment 120 features an offset hinge 122 similar to the offset hinge 102 of the first alternative primary segment 100 (FIG. 16). The third alternative primary segment 120 additionally includes undulating overlapping tapering surfaces 124 for portions of the top and bottom structures of the third alternative primary segment 120 adjacent the distal end. These undulating overlapping tapering surfaces 124 can be spread apart by longitudinal advancement of a first alternative shim 126 which is preferably cylindrical and as wide as the entire segment 120. As the first alternative shim 126 is advanced (along arrow P of FIG. 19) it passes through a series of steps corresponding with different stages of lordosis which can be provided to the intervertebral space S (FIG. 1).

Because the tapering surfaces 124 undulate, a series of locations are provided where the first alternative shim 126 can come to rest. Varying degrees of height adjustment corresponding to various different degrees of lordosis can thus be provided to the intervertebral space S (FIG. 1). The first alternative shim 126 can be advanced by being pushed along through an access passage 128 with any appropriate form of pushing tool, or could be advanced with a threaded pin similar to the advancement of the wedge 86 along the pin 82 of the secondary segment 60 of the preferred embodiment.

Because the tapering surfaces 124 overlap, a greater amount of height increase at the distal end of the third alternative primary segment 120 is provided (see FIG. 20). This third alternative primary segment 120 height magnification system could be fitted on an alternative secondary segment having a neck rather than a tunnel in a relatively straightforward fashion due to the relatively low profile passage 128 which could pass through a neck without compromising a strength of the neck in such an alternative secondary segment. Hence, this height magnification system is merely illustrated in the context of primary segment for convenience, but could be equally well incorporated into a secondary segment.

With particular reference to FIGS. 22–27, details of a fourth alternative primary segment are described. The fourth alternative primary segment 130 is configured to allow height adjustment both at a distal end of the fourth alternative primary segment 130 and at a proximal end of the fourth alternative primary segment 130. Specifically, the top and bottom portions of the fourth alternative primary segment 130 are preferably joined together with an expanding hinge 132.

Function of the expanding hinge is shown in detail in FIGS. 24–27. The expanding hinge 132 includes two separate pintles 134 on opposite sides of a longitudinal passage extending through the fourth alternative primary segment 130. The pintles 134 reside within slots 136. Hence, the expanding hinge 132 allows both rotation and vertical expansion (along arrow R of FIGS. 25 and 26) while still holding the top and bottom portions of the fourth alternative primary segment 130 together.

A longitudinal passage passing through the fourth alternative primary segment includes a proximal recess 140 near a proximal end of the fourth alternative primary segment 130. A proximal shim 142 can be advanced along a guide wire in a manner similar to the advancement of the shim 50 of the primary segment 20 of the preferred embodiment. The proximal shim 142 is preferably configured with a contour matching that of the proximal recess 140. Hence, as the proximal shim 142 is advanced into the passage (along arrow Q of FIG. 22), the proximal shim 142 expands the top and bottom portions of the fourth alternative primary segment 130 away from each other until the proximal shim 142 rests within the proximal recess 140.

As an alternative to providing the proximal recess 140, the proximal shim 142 could merely have a tapering contour (shown in FIG. 22) and the friction between tapering surfaces of the proximal shim 142 and upper and lower surfaces of the pathway within the fourth alternative primary segment 130 could allow the proximal shim 142 to remain in a position where it has been advanced unless specific forces are applied to the proximal shim 142.

Figure 22:
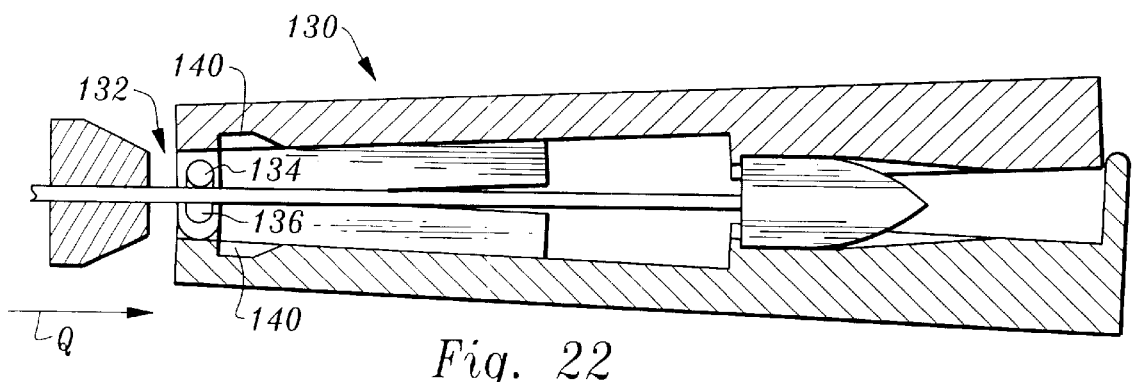
FIG. 22 is a full sectional side elevation view of a fourth alternative embodiment of a primary segment of the implant assembly of this invention showing a guide wire with both a shim advanced past a tunnel in the fourth alternative primary segment and a proximal shim and expanding hinge to allow height expansion of a proximal end of the fourth alternative primary segment of the implant assembly of this invention.
Figure 23:
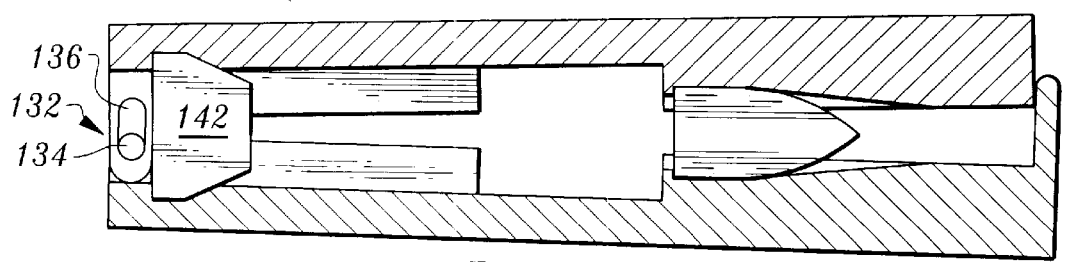
FIG. 23 is a full sectional side elevation view of that which is shown in FIG. 22 after insertion of the proximal shim of this embodiment into a proximal recess to enhance the proximal height of the fourth alternative primary segment of the implant assembly of this invention.
Figure 24:
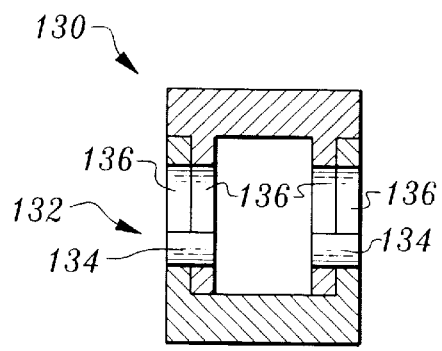
FIGS. 24–27 are sectional and side elevation views of an expanding hinge of the fourth alternative primary segment of the implant assembly of this invention revealing in detail the various stages in the operation of this expanding hinge.
Figure 26:
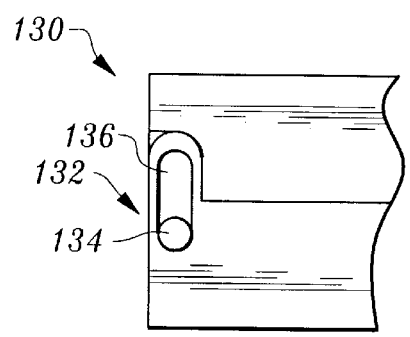
Figure 25:
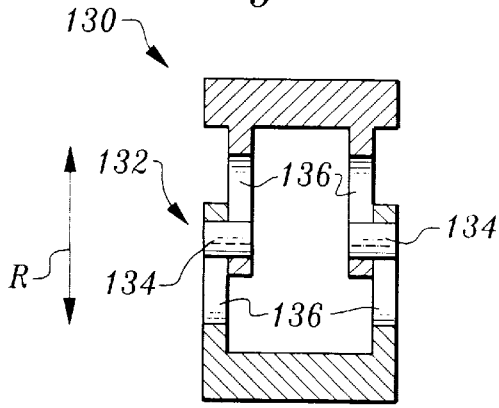
Figure 27:
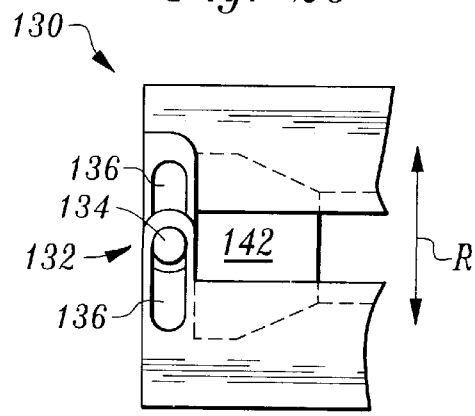

As shown in FIG. 22, a shim similar to the shim 50 of the preferred embodiment would first be advanced along the guide wire into the tapering end of the passage within the fourth alternative primary segment 130. The proximal shim 142 would then be advanced into the passageway. Hence, the fourth alternative primary segment 130 experiences height magnification both adjacent a distal end and adjacent the proximal end of the fourth alternative primary segment 130. The proximal shim 142 could similarly be used with an expanding hinge 132 fitted into the proximal second end 68 of the secondary segment 60 to give the secondary segment 60 proximal end 68 height adjustability.

FIG. 28 shows a fifth alternative primary segment 150 which uniquely includes beveled tunnel sides 152. These beveled tunnel sides 152 allow a second alternative secondary segment 155 to pass through the tunnel in a nonperpendicular direction. Specifically, the secondary segment 155 can be angled relative to the fifth alternative primary segment 150 by an angular amount (arrow X of FIG. 28) which can be less than or greater than 90°, rather than only exactly 90°. Angle X in FIG. 8 is shown at approximately 60° but could be reduced to as little as 45° or less and still allow the secondary segment 155 to pass through the tunnel in the fifth alternative primary segment 150 without being blocked by the beveled tunnel sides 152. The beveled tunnel sides 152 are shown angled approximately 45° away from an orientation perpendicular to a long axis of the fifth alternative primary segment 150. However, the angles of the beveled tunnel sides 152 and the angle X that the secondary segment 155 shares relative to the fifth alternative primary segment 150 could be increased or decreased depending on the needs of the medical practitioner for the implant assembly 10.

The second alternative secondary segment 155 preferably includes a relief bevel 156 (FIG. 28) which allows a side wall of the neck in the second alternative secondary segment 155 to come into contact with a side surface of the first alternative primary segment 150 after the second alternative secondary segment 155 has been rotated into its final position. The relief bevel 156 thus allows the second alternative secondary segment 155 and the fifth alternative primary segment 150 to more completely stabilize each other in a fully interlocking fashion so that the implant assembly 10 stabilizes the intervertebral space S (FIG. 1) as completely as needed.

A sixth alternative primary segment 160 is shown in FIG. 29 which includes relief notches 162 in sides of the sixth alternative primary segment 160 adjacent the tunnel. The relief notches 162 are an alternative to the relief bevel 156 of the embodiment of FIG. 28. Specifically, FIG. 29 illustrates how either the relief bevel 156 can be provided on the second alternative secondary segment 155 or relief notches 162 can be provided as in the sixth alternative primary segment 160 so that complete rotation of the third alternative secondary segment 164 can be achieved without the necessity of the relief bevel 156 of the second alternative secondary segment 155. Of course a combination of the relief bevel 156 and the relief notches 162 could be resorted to so that abutting surfaces of the primary segment and the secondary segment could mesh together in a manner providing stability for the overall implant assembly 10.

A fourth alternative secondary segment 170 is shown in FIG. 30 along with the fifth alternative primary segment 150. This implant assembly shown in FIG. 30 is shown with the first alternative primary segment 150 in section and clearly illustrating how the fourth alternative secondary segment 170 can fit through the tunnel in the fifth alternative primary segment 150 at an angle X (FIG. 28) other than perpendicular and be rotated, about arrow T, and to the final position such as that shown in FIG. 28.

It can be seen from FIG. 30 that not all of the beveled tunnel sides 152 are strictly necessary for the passage of the fourth alternative secondary segment 170 through the tunnel in the fifth alternative primary segment 150. By providing the beveled tunnel sides 152 in two directions, the fifth alternative primary segment 150 becomes reversible. However, inclusion of both beveled tunnel sides 152 would not be absolutely necessary. Rather, only one beveled tunnel side 152 could be provided on each side of the tunnel and other beveled tunnel sides 152 could be eliminated. Particularly, and as shown in FIG. 30, the beveled tunnel sides 152 which include reference numerals thereon could be removed and the fourth alternative secondary segment 170 could still pass through the tunnel in the fifth alternative primary segment 150 successfully.

Selective relief bevels 172 similar to the relief bevels 156 (FIG. 28) could be provided on some of the neck side walls, but would not need to be on all neck side walls. The selective relief bevels 172 would come to rest adjacent sides of the primary segment 150 after rotation about arrow T and provide enhanced stability between the segments 150, 170.

This disclosure is provided to reveal a preferred embodiment of the invention and a best mode for practicing the invention. Having thus described the invention in this way, it should be apparent that various different modifications can be made to the preferred embodiment without departing from the scope and spirit of this disclosure. For instance, while the primary segment 20 and the secondary segment 60 are described in the preferred embodiment as being expandable, a simplified variation of this invention would not require such expandability. When structures are identified as a means to perform a function, the identification is intended to include all structures which can perform the function specified.

What is claimed is:

1. An implant for surgical placement within an intervertebral space, during a spinal fusion procedure, the implant comprising in combination:
    a primary segment having an elongate form between a distal end and a proximal end;
    a secondary segment having an elongate form between a first end and a second end; and
    a portion of said secondary segment between said first end and said second end crossing said primary segment between said distal end and said proximal end.

2. The implant of claim 1 wherein both said primary segment and said secondary segment have a height between a top surface and a bottom surface which is greater than a width between lateral sides of said segments, such that rotation of said segments about a long axis from an orientation where said top surface is laterally spaced from said bottom surface to an orientation where said top surface is above said bottom surface results in an increase in height of both said segments.

3. The implant of claim 1 wherein at least a portion of at least one of said segments is open sufficiently to allow the other of said segments to pass at least partially through said open portion, such that said segments are at least partially interlocking together.

4. The implant of claim 3 wherein said open portion is sufficiently large that said segments are substantially coplanar.

5. The implant of claim 4 wherein a height of said primary segment between a top surface and a bottom surface is equal to a height of said secondary segment between a top surface and a bottom surface with said top surface of said primary segment coplanar with said top surface of said secondary segment and said bottom surface of said primary segment coplanar with said bottom surface of said secondary segment.

6. The implant of claim 3 wherein said primary segment is at least partially open between said distal end and said proximal end and said secondary segment is at least partially open between said first end and said second end, said opening in said primary segment adjacent said opening in said secondary segment where said secondary segment crosses said primary segment, such that said primary segment and said secondary segment are at least partially interlocking together.

7. The implant of claim 6 wherein said opening in said primary segment is a tunnel between a top surface and a bottom surface, said tunnel at least as large as at least a portion of said secondary segment between said first end and said second end, such that said second segment can be located extending through said tunnel.

8. The implant of claim 7 wherein said secondary segment includes a neck between said first end and said second end, said neck having a lesser height between a top surface of said secondary segment and a bottom surface of said secondary segment than a height of other portions of said secondary segment adjacent said neck, said neck having a height less than a height of said tunnel in said primary segment, such that said neck of said secondary segment can be located extending through said tunnel in said primary segment.

9. The implant of claim 1 wherein said primary segment includes a top structure and a bottom structure, said top structure and said bottom structure movable relative to each other, such that a height of said primary segment can be modified.

10. The implant of claim 9 wherein said primary segment includes a spacer between said top structure and said bottom structure, said spacer moving said top structure away from said bottom structure to increase a height of said primary segment.

11. The implant of claim 10 wherein said spacer is a shim having a tip with a lesser height than a tail, said primary segment including a passage extending at least partially through said primary segment between said top structure and said bottom structure, said passage having a lesser height in a tapering region, said tapering region closer to said distal end than to said proximal end, said shim having a height greater than a height of said passage at said tapering region, such that said shim pushes said top structure away from said bottom structure when said shim is moved through said passage into said tapering region.

12. The implant of claim 9 wherein said top structure and said bottom structure are hinged together at a location on said primary segment closer to said proximal end than to said distal end.

13. The implant of claim 12 wherein said second segment includes a top jaw and a bottom jaw, said top jaw movable relative to said bottom jaw, said top jaw and said bottom jaw hinged together at a location closer to said second end of said secondary segment than said first end of said secondary segment.

14. The implant of claim 13 wherein said hinge in said primary segment and said hinge in said secondary segment are each expansion hinges which allow both pivoting and vertical translation of portions of said structures adjacent said hinge.

15. An implant for an intervertebral space, the implant comprising in combination:
 a primary segment having an elongate form between a distal end and a proximal end;
 a second segment having an elongate form between a first end and a second end;
 a portion of said second segment between said first end and said second end intersecting said primary segment between said distal end and said proximal end;
 said primary segment including a tunnel passing laterally therethrough between said distal end and said proximal end;
 said tunnel having a height less than a height of said primary segment;
 said secondary segment including a neck between said first end of said secondary segment and said second end of said secondary segment;
 said neck having a height less than portions of said secondary segment adjacent said neck; and
 said neck having a height at least as small as a height of said tunnel in said primary segment, such that said neck in said secondary segment can be located extending through said tunnel in said primary segment.

16. The implant of claim 15 wherein said neck of said secondary segment is sized to allow said secondary segment to rotate at least 90° about a long axis of said secondary segment while said neck of said secondary segment is within said tunnel in said primary segment.

17. The implant of claim 16 wherein said primary segment includes a top structure and a bottom structure, said top structure hingedly attached to said bottom structure at a location closer to said proximal end than to said distal end, and said secondary structure having a top jaw hingedly attached to a bottom jaw at a location on said secondary segment closer to said second end than to said first end.

18. An intervertebral space implant comprising in combination:
 a primary segment having an elongate form between a distal end and a proximal end;
 a second segment having an elongate form between a first end and a second end;
 a portion of said second segment between said first end and said second end crossing said primary segment between said distal end and said proximal end; and
 at least one of said segments at least partially open at a location between ends thereof, such that said primary segment and said secondary segment are at least partially interlocking where said segments cross.

19. The implant of claim 18 wherein both said primary segment and said secondary segment include an at least partially open region between ends thereof.

20. The implant of claim 18 wherein said primary segment includes a tunnel passing laterally therethrough between said distal end and said proximal end, said secondary segment including a neck between said first end and said second end, said neck in said secondary segment sized sufficiently small to pass through said tunnel in said primary segment.

* * * * *